United States Patent [19]

Shoyab et al.

[11] Patent Number: 5,093,045
[45] Date of Patent: Mar. 3, 1992

[54] BIOLOGICALLY ACTIVE LIPIDS BINDING MEMBRANE RECEPTORS

[75] Inventors: Mohammed Shoyab; George J. Todaro, both of Seattle, Wash.

[73] Assignee: Oncogen, Seattle, Wash.

[21] Appl. No.: 494,925

[22] Filed: Mar. 13, 1990

Related U.S. Application Data

[63] Continuation of Ser. No. 45,691, Apr. 30, 1987, abandoned, which is a continuation of Ser. No. 638,811, Aug. 8, 1984, abandoned.

[51] Int. Cl.$^5$ ............................................. C11C 3/02
[52] U.S. Cl. .................................. 260/410.8; 260/412
[58] Field of Search .......................... 260/410.8, 412

[56] References Cited

U.S. PATENT DOCUMENTS

| | | | |
|---|---|---|---|
| 3,000,748 | 9/1961 | Clark | 260/410.8 |
| 3,029,147 | 4/1962 | Radlove . | |
| 3,748,348 | 7/1973 | Baratham | 260/410.7 |

OTHER PUBLICATIONS

Shoyab et al., *Journal of Biological Chemistry*, vol. 256, No. 23, 12/10/81, pp. 12529-12534.
Markley, Klare, *Fatty Acids—Their Chemistry, Properties Production and Uses*, Part I, 1960, p. 334.
Welsh et al., *Chemical Abstracts*, vol. 96, 50892v, 1982.
Laher et al., *Chemical Abstracts*, vol. 99, 65605q, 1983.
Welsh et al., *J. Food Safety* (1981) 3(2):99-107.

*Primary Examiner*—Lester L. Lee
*Assistant Examiner*—E. J. Kraus
*Attorney, Agent, or Firm*—Morrison & Forester

[57] ABSTRACT

Neutral lipids are provided characterized by binding to phorboid and ingenoid receptors. These lipids are found in a wide variety of cellular sources as well as milk and may be isolated by specific extraction and chromatographic procedures. Depending upon the source, the glycerides may be mono- or di-glycerides, wherein the total number of carbon atoms of the fatty acis is in the range of 18 to 26, so that the monoglyceride has a fatty acid of at least 18 carbon atoms, while the di-glyceride has a fatty acid of at least 14 carbon atoms. The long chain fatty acids have at least one site of olefinic unsaturation.

2 Claims, No Drawings

BIOLOGICALLY ACTIVE LIPIDS BINDING MEMBRANE RECEPTORS

This application is a continuation of application Ser. No. 07/045,691, filed Apr. 30, 1987, now abandoned which is a continuation of application Ser. No. 638,811, filed Aug. 8, 1984, now abandoned.

BACKGROUND OF THE INVENTION

1. Field of the Invention

The role of lipids in cellular growth, differentiation, and activity, is a broad and extensive one. Fatty acids are found in membranes and show a wide variety of hormonal functions. Prostaglandins, thromboxanes, prostacyclin and leukotrienes are illustrative of lipid compounds which have a broad spectrum of physiological properties. These compounds are as a result of oxidation of arachidonic acid and are referred to as eicosanoids.

The eicosanoids are extremely potent, ubiquitous agents with numerous bewildering actions: effect on muscle contraction, platelet aggregation, leukocyte migration and gastric secretion. Lipid compounds which can affect or modulate the arachidonic acid cascade can provide potent physiological agents.

The existence of receptors having specific affinity for the plant derived phorbol and ingenol ester compounds suggests that the naturally occurring receptors recognize endogenous ligands which have some structural similarity to phorboids and ingenoids. Prior attempts to isolate and characterize such ligands that interact with these receptors have been unsuccessful, due in part to the existence of phorbol ester binding protein and phorbol diester hydrolase.

It would therefore be of great interest to be able to find either the endogenous ligands or other compounds, differing in minor ways from the endogenous ligands, which would provide for one or more of the biological activities, particularly the physiological activities, of the endogenous ligands.

2. Description of the Prior Art

Dredger and Blumberg, *Proc. Natl. Acad. Sci. USA* (1980) 77:567-571; Shoyab and Todaro, *Nature* (1980) 288:451-455 and Shoyab et al., *Carcinogenesis* (1981) 2:1273-1276 report the existence of specific high affinity receptors for biologically active phorbol and ingenol esters in a variety of cells and tissues. The difficulties associated with isolating and characterizing ligands that interact with phorboid receptors and induce 12-O-tetradecanoylphorbol-13-acetate ("TPA") like affect in target cells have been reported by Shoyab and Todaro, *J. Biol. Chem.* (1982) 257:439-445 and Shoyab et al., ibid. (1981) 256:12529-12534.

SUMMARY OF THE INVENTION

Lipids are provided which bind to phorboid receptors and are competitive with phorbol and ingenol esters for the specific receptors. The compounds are characterized by being mono- and di-glycerides, having a total fatty acid content of at least 18 carbon atoms and having at least one site, normally at least two sites of ethylenic unsaturation. The compounds find use in vitro in assays, isolation of receptors, and diagnosis. The compounds are isolated from naturally occurring sources by an extraction and chromatographic regimen.

DESCRIPTION OF THE SPECIFIC EMBODIMENTS

Lipids are provided having phorbol and/or ingenol receptor binding affinity, which lipids are capable of competing for phorbol esters for the natural cellular receptors. The lipids are characterized by being mono- or di-glycerides (having at least one free hydroxyl), where the total fatty acid content is at least 18 carbon atoms and not more than 24 carbon atoms. Either or both the first and second carbon atoms of glycerol may be ester substituted. There will be at least one site, usually at least two sites of ethylenic unsaturation, and generally not more than four sites, more usually not more than three sites of ethylenic unsaturation. The sites of unsaturation may be varied, where the double bonds may be conjugated or non-conjugated, usually non-conjugated. The molecular weight of the glyceride will generally be in the range of from about 356 to about 454. The lipids are free of other contaminants, such as cellular debris, other lipids lacking the binding activity, proteins, and saccharides. Generally, the lipid composition will be at least 90% of lipids having the receptor binding activity, usually at least 95%, and preferably the activity being represented by not more than three components, preferably from 1 to 2 compounds.

The lipids fall into two groups: (a) naturally occurring lipids or ligands referred to as endogenous lipids or ligands ("EL"), which may include one or a plurality of compounds, usually not more than three compounds, generally having the same number of carbon atoms and differing as to sites of ethylenic unsaturation; and (b) synthetic ligands or lipids ("SL") which are characterized by being able to mimic some of the physiological activity of the EL, compete with phorbol and ingenol esters for their receptors, and display other activities which find use in vitro.

Among the EL compounds are two different groups: (1) ELs obtained from tissues; and (2) ELs obtained from milk. The two groups of ELs have common characteristics in being glycerides, being capable of inhibiting the activity of phorbol dibutyrate binding to natural receptors and having a total fatty acid content of at least 18 carbon atoms, although the fatty acids differ substantially, since the tissue-derived EL (EL1) is a monoglyceride and the milk-derived EL (EL2) is a di-glyceride.

The group of compounds concerned with the tissue-derived EL1 will be considered first. These compounds are found in accordance with the isolation technique in order of diminishing amount in the following tissue: pancreas, intestine, stomach, testicles, brain, kidney, liver, muscle, spleen, lung and heart. The compounds are characterized by being mono-glycerides having a fatty acid of 18 or 20 carbon atoms, wherein the fatty acid may be at either the 1 or 2 position of glycerol.

EL1 is further characterized that under high pressure chromatographic analysis, employing a silica gel column in a continuous linear gradient with petroleum ether as the primary solvent and methanol as the secondary solvent, the major fraction of EL1 has a similar retention time or spectrum to monolinolein. On a thin layer chromatograph, employing a developing solution of hexane/ethyl ether/acetic acid (60:40:1), again, EL1 shows a similar development to monolinolein.

The physiological characteristics of EL1 includes stimulation of protein kinase activity, where the kinase is a serine protein kinase, isolated from murine brain and acts as a phorboid receptor. As already indicated, EL1 can compete with phorbol dibutyrate to inhibit binding phorbol dibutyrate to its receptor.

EL1 is chemically characterized by being resistant to the action of phospholipase and lipoxygenase. EL1 is sensitive to lipase, hydrogenation, acetylation, and alkaline hydrolysis and methanolysis. The receptor binding activity is reversibly sensitive to acetylation, losing activity upon acetylation which can be at least partially recovered upon mild hydrolysis.

The EL1 activity can be obtained from homogenized tissue, e.g., intestinal tissue, pancreatic tissue, or the like, ensuring complete lysis and dispersion of the cells, followed by removal of cellular debris. The aqueous supernatant may then be extracted with a chloroform-methanol extractant, with the solvents at about a 1:1 volume ratio. After concentration by evaporation, the residual non-lipids may be extracted with dilute saline, particularly about 0.8–1.0 M saline. The remaining residue is a crude lipid composition.

The crude lipid composition may then be extracted with acetone at a ratio of about 1 ml acetone per gram of starting tissue. The acetone extract may then be chromatographed on a silica gel column, e.g., Florisil, at a moderate rate (100–200 ml per hour), using an increasingly polar eluent, with the primary solvent being ethyl ether and the secondary solvents being hexanes, methanol and acetic acid. The ethyl ether-hexane mixture will generally be about 1:1, while only minor amounts, less than five volume percent and more than one volume percent of methanol and acetic acid will be used. The major amount of the EL1 is found in the ethyl ether-methanol fraction.

Further purification can be achieved using high pressure liquid chromatography employing a silica gel column, e.g., Porasil. Conveniently, a continuously linear gradient is employed, using petroleum ether as the primary solvent and methanol as the secondary solvent, with the gradient ranging from 0 to 30% methanol. The various fractions may be monitored by receptor binding activity. To further enhance the purification, the fractions containing the major amount of activity may be combined, the solvent evaporated, and the procedure repeated. The product may then be stored for further use. The product will have a specific activity of at least 1200ng PDBu equivalent/mg, usually at least 1400ng PDBu equivalent/mg.

The EL2 is a di-glyceride having a fatty acid of even number carbon atoms of from 14 to 18 carbon atoms and a lower molecular weight even number fatty acid of from 4 to 6 carbon atoms. The higher molecular weight fatty acyl groups are at position 1, while the lower molecular weight fatty acyl groups are at position 2. EL2 compositions are capable of competing with phorbol dibutyrate for the membrane receptor.

Upon chromatography on silicic acid, using 1:3 ethyl ether/petroleum ether; 1:1 ethyl ether/petroleum ether and ethyl ether, most of the EL2 activity was found in the ethyl ether fraction. EL2 does not stimulate the arachidonic acid cascade, as evidenced by EL1.

In addition to EL1 and EL2, known lipids may also be used for binding to phorboid receptors. These lipids include 1-monopalmitolein, 1-monolinolein, and 1-monoarachidonin. These glycerides are shown to compete with phorbol dibutyrate for its receptor and to stimulate the arachidonic acid cascade.

The subject glycerides may find a variety of uses. In vitro, the subject glycerides may be used as ligands in diagnostic assays for determination of the presence of the endogenous ligands. EL1 and EL2. In addition, they may be used as haptens for conjugation to antigens to provide an immunogen for the production of polyclonal or monoclonal antibodies specific for EL activity. The subject glycerides may also be used for titrating the presence of receptors, may be used with affinity columns for isolation of receptors, purification of kinases having appropriate receptor sites, or in cell cultures for stimulating the arachidonic acid cascade for the production of eicosanoids. Thus, the subject compounds may be used to enhance the production of eicosanoids from a particular cell culture, which has been selected, by mutagenesis, transformation, transfection or the like, as an overproducer of one or more of the eicosanoids.

With neoplastic cells, the subject compounds may be used as modulators of growth, differentiation and cellular communication. Thus, they may serve as inhibitors of tumor promotion or inhibiting the proliferation of neoplastic cells either by themselves or in conjunction with other anti-cancer agents. The subject compounds may interact with oncogene-proteins and alter their biological activity.

The ability to modify the arachidonic acid cascade may result in the ability to modulate platelet and leukocyte function, immune response and synaptic and neuroeffector functional sites.

The following examples are offered by way of illustration and not by way of limitation:

EXPERIMENTAL

Materials and Methods

Materials

Phorbol and its derivatives were purchased from CMC Cancer Research Chemical, Inc. (Brewster, N.Y.). Lipids were bought from Sigma (St. Louis, Mo.), Nu-Crek-Prep, Inc. (Elysian, Minn.), Supelco, Inc. (Bellefonte, Pa.) and Avante Polar Lipids, Inc. (Birmingham, Ala.). Biochemicals and enzymes were purchased from Sigma (St. Louis, Mo.) or Cal. Biochem (La Jolla, Calif.). Phorbol dibutyrate (PDBu) was labeled with [$^3$H] at position 20 to a specific activity of 4.9 Ci/mmol, as described previously. Other labeled chemicals were from New England Nuclear (Boston, Mass.). All other chemicals were reagent grade or better and were obtained from commercial suppliers.

Preparation of Murine Brain Membranous Fraction (BMF)

Pooled murine brains from approximately 2 month old mice, NFS strain, were minced with scissors, suspended in 1 mM triethanolamine-HCl, pH 7.4, and disrupted with a polytron P-10 (Brinkman). This and all subsequent steps were performed at 4° C. The homogenate was centrifuged for 10 minutes at 1700xg; the supernate was removed and centrifuged for 60 minutes at 105,000xg. The resulting pellet was suspended in one-fourth of the initial volume of PBS. The suspension was aliquoted into a small volume and stored at −70° C.

PDBu Binding Assay

The binding of $^3$H-PDBu to BMF or soluble receptors was performed in duplicate in 12×75mm disposable glass tubes (Kimax) both in the absence and presence of 20μg/ml unlabeled PDBu; the binding mixture contained 5ng of $^3$H-PDBu (4×10$^4$cpm), 0.2% final concentration of DMSO and BMF (50μg protein) or soluble receptors in a total volume of 0.25 ml binding buffer (BB) consisting of Dulbecco's minimum essential medium (DMEM) containing bovine serum albumin (BSA 1mg/ml) and N,N,-bis-(2-hydroxyethyl)-2-aminoethane sulfonic acid (BES, 5mM), adjusted to pH 6.8. After incubation for 30 minutes at 23° C. the tubes were chilled, 0.5 ml cold 4% calf serum (Colorado Serum Co., Denver, CO) and 0.7 ml cold polyethylene glycol (PEG 6,000) in 1 mM Tris-HCl, pH 7.4 was added to each tube, the contents vortexed, the tubes allowed to stand for 15 min at 4° C., and centrifuged for 10 min at 1500xg at 4° C. The supernatant solution was carefully aspirated off, the pellet suspended in 2.5 ml of cold 10% PEG in 0.1 M Tris-HCl, pH 7.4, containing 0.5% SDS and 1 mM EDTA). The mixture was transferred to counting vials and 10 ml of Aquassure (NEN) was added to each vial. The vials were vigorously shaken and radioactivity determined using a Beckman beta counter. The radioactivity bound in the presence of $20\mu g/ml$ (50–200cpm) unlabeled PDBu was considered to be nonspecific and all data were corrected accordingly.

Assays for PDBu Binding Inhibiting Activity (PBIA)

The loss of the ability of $^3$H-PDBu to bind to receptors in the presence of ligand was used as the measure of inhibiting activity. PDBu binding inhibition assays were performed as described above, except the test materials were added to the reaction mixture and binding measured as described above.

Calculation of ng PDBu Equivalent (ng equivalent)

The PBIA of ligand was equated with that of PDBu by the use of the term ng equivalent calculated from a plot of [$^3$H]PDBu bound versus the log molar concentration for several biologically active phorbol esters (2). The curve corresponding to PDBu inhibition of PDBu binding was used by reading the molar concentration corresponding to the percent of control binding of $^3$H]PDBu in the presence of ligand to obtain the units ng PDBu equivalent of ligand.

Gel Filtration Assay for PDBu Binding

The reaction mixture consisting of 2.5ng of $^3$H]PDBu (~20,000cpm), 0.5% final concentration of DMSO, 0 or $5\mu g$ of unlabeled PDBu and soluble receptors or binding protein in a total volume of 0.125 ml was incubated for the desired time and temperature. The mixture was applied to a column of Bio-Gel P-10 (0.9×7.9cm) previously equilibrated with phosphate-buffered saline (pH 7.1) at 4° C. The flow rate was maintained at approximately 10 ml/h, 10-drop fractions were collected and radioactivity determined as described above.

Assay for Protein Kinase

In a final volume of 0.25 ml, the reaction mixture in duplicate contained $5\mu mol$ Tris-HCl (pH 7.4), $1\mu mol$ $MgCl_2$, $50\mu g$ histone, 0.12nmol [$-^{32}P$] ATP ($8\times10^6$cpm at arrival) and an appropriate amount of purified receptor protein. The reaction was carried out for 15 min at 23° C. The phosphorylated proteins were precipitated with 5% cold TCA, using BSA ($250\mu g$) as carrier. The mixture in the tubes was allowed to settle at 4° C. for 15–30 min. Precipitates were collected on cellulose nitrate filters ($0.45\mu m$) and washed with 75 ml of cold 5% TCA. Filters were dried and counted in Betafluor scintillation fluid.

Isolation of Ligands. Preparation of Crude Lipids from Murine Intestine and Other Tissues Female ex-breeder BALB/c mice were sacrificed by carbon dioxide exposure and their intestine and various other tissues were removed and placed on ice. The intestines were then cleaned with approximately 6–10 ml of cold PBS per intestine using a blunt end 19 gauge needle and 6 ml syringe. One hundred and twenty grams of intestines were then homogenized in 600 ml of cold double distilled water using a Waring blender. This homogenate was polytroned for one minute at 4° C. using a Brinkman Polytron set at full speed and then centrifuged at 400xg for 20 minutes. Following centrifugation approximately 260 ml of supernatant was decanted and to this was added 1400 ml of 1:1 chloroform/methanol. This was gently mixed and then centrifuged at 580xg for 10 minutes. The chloroform/methanol layer was then removed and was evaporated under nitrogen to a volume of approximately 200 ml. An equal volume of 0.9M NaCl was added, the mixture was mixed and then centrifuged at 580xg for 10 minutes. The chloroform/methanol layer was then removed and re-extracted with 0.9M NaCl. Following the second extraction the chloroform/methanol layer was evaporated under nitrogen in a 37° C. water bath. The remaining residue was referred to as crude lipid.

Acetone Extraction of Crude Lipid

One hundred and twenty ml of acetone was added to the crude lipid (1 ml acetone per gram of starting tissue), vigorously mixed, and centrifuged at 615xg for 5 minutes to pellet the precipitates. The supernatant was carefully decanted and then evaporated under nitrogen in a 37° C. water bath. This was referred to as the acetone extract.

Florisil Chromatography

A glass column fitted with a Teflon stopcock was packed with Florisil (60–100 mesh, Sigma Chemical) to a bed size of 2.5cm×21cm. A separatory funnel connected to the column top via a ground-glass joint served as a reservoir for eluting solvent. The acetone extract was dissolved in 10 ml of hexanes and added carefully from a pipette so as not to disturb the surface of the adsorbant. The stopcock was then opened allowing the lipid solution to pass into the adsorbant, and during elution a head of solvent was maintained to prevent the surface of the adsorbant from being disturbed. The following stepwise elution schedule was performed at a flow rate of 150 ml/hr using 200 ml of each solvent:
  Step I:hexanes
  Step II:ethyl ether:hexanes (5:95)
  Step III:ethyl ether:hexanes (15:85)
  Step IV:ethyl ether:hexanes (25:75)
  Step V:ethyl ether:hexanes (50:50)
  Step VI:ethyl ether methanol (98:2)
  Step VII:ethyl ether:acetic acid (96:4)
  Step VIII:methanol These fractions were prepared for determining their PDBu binding inhibiting activity by nitrogen evaporation; dissolving the residue in 10 ml chloroform and extracting it with an equal volume of sodium chloride and processing it as described. The residue remaining following evaporation was dissolved in 1 ml of acetone and $25\mu l$ was evaporated and assayed.

Following the establishment of the fraction corresponding to activity, the Florisil elution schedule was modified by following sample application to the column proceeding directly to Steps V-VIII using 250 ml of solvent for Step V and 200 ml for the subsequent steps. Most of the activity was eluted in fraction VI.

High Pressure Liquid Chromatography (HPLC) of Florisil Chromatography Fraction VI The following instrumentation manufactured by Waters Associates, Inc. (Milford, Mass.) was used to perform the HPLC: 2 model 6000A solvent delivery systems, U6K injector, model 440 variable wavelength detector set for 235nm and a model 660 solvent programmer. Separation was carried out using a Porasil (Waters Associates, Inc.) 3.9mm i.d.×30 cm stainless steel column at 24° C. using a water jacket connected to a Haake circulating water bath. A continuous linear gradient was used between the primary solvent petroleum ether and the secondary solvent methanol. The gradient conditions were 0 to 30% methanol in one hour at a constant solvent flow rate of 1 ml/min. All solvents were HPLC grade. The sample was dissolved in petroleum ether for injection. 4000ng PDBu equivalent lipid in petroleum ether was applied in each run. One ml fractions were collected.

Following the chromatography, an aliquot was taken from every fraction and assayed for PBIA as described. The fraction containing the activity was then evaporated under nitrogen, dissolved in 400μl petroleum ether and re-chromatographed on the HPLC using the conditions described above. Fraction collection was performed by manual collection of peaks during this second chromatographic step. All fractions were again aliquoted and assayed for PBIA. The fraction corresponding to the activity was then evaporated under nitrogen, suspended in chloroform, blanketed with nitrogen and stored at −70° C. This was the fraction used for characterization of the PDBu binding inhibiting activity unless stated otherwise.

The same protocol was followed to purify endogenous ligands from other tissues, such as pancreas and stomach.

Preparation of Crude Lipid from Cow Milk

Cow's milk (fresh and commercial) was defatted by centrifugation at 10,000xg for 30 minutes. The resultant lower defatted layer of milk was then carefully removed and 2.5 times volume of 2:1 chloroform/methanol was added. This was gently mixed and then centrifuged at 580xg for 10 minutes. The chloroform/methanol layer was evaporated to a volume of approximately 200 ml. Sodium chloride extractions were then performed as described above.

Acetone Extraction of Crude Milk Lipid

One ml of acetone was added per 100 ml of chloroform/methanol extract, the sample was vigorously mixed, and centrifuged at 615xg for 5 minutes to pellet the precipitate. The supernatant was carefully decanted and then evaporated under nitrogen in a 37° C. water bath.

Silicic Acid Chromatography of Acetone Extracted Milk Lipid

A glass column fitted with a Teflon stopcock was packed with silicic acid to a bed size of 2.5×21cm. The solvent elution apparatus was as described above. The acetone extract was dissolved in a minimal volume of petroleum ether and then carefully added to the top of the column. The following stepwise elution schedule was performed at a flow rate of 150 ml/hr using 250 ml of each solvent: 25% ethyl ether in petroleum ether, 50% ethyl ether in petroleum ether, and 100% ethyl ether. The resultant fractions were nitrogen evaporated and assayed for PBIA as described previously. Most of the PBIA was eluted in the 100% ethyl ether fraction.

High Pressure Liquid Chromatography of 100% Ethyl Ether Silicic Acid Chromatography Fraction Approximately 3000ng PDBU equivalent milk lipid (silicic acid chromatography 100% ethyl ether fraction) was dissolved in 800μl acetone. The sample was then clarified by centrifugation at 1500xg for 5 minutes prior to injection onto a 3.9mm×30cm fatty acid analysis column (Waters Associates, Inc.) that was temperature controlled to 37° C. The primary solvent was water and the secondary solvent was acetonitrile. The gradient conditions were 0 to 50% acetonitrile in 15 minutes, and then 50 to 100% acetonitrile in 1 hour at a constant solvent flow rate of 1 ml/min. U.V. absorbance was monitored at 260 mm. Following chromatography the fractions were assayed for PBIA as described. Storage of crude and purified milk lipid was as described for lipid from murine intestine.

Phospholipase Treatment

Phorbol binding inhibiting lipid (PBIL) was suspended in DMSO and two incubation conditions were used for each phospholipase: (1) 300ng eq. of PBIL in 400μl DMSO +100μl of enzyme (lmg/ml in PBS with $Ca^{++}$ and $Mg^{++}$ +1900μl of PBS with $Ca^{++}$ and $Mg^{++}$; (2) same as (1) except enzyme was omitted. Incubation was for 1 hr at 37° C. Following incubation 5 ml of 2:1 chloroform/methanol was added, mixed, and centrifuged at 580xg for 10 minutes, and the organic (lower) layer was removed and evaporated under nitrogen. The remaining residue was dissolved in 70μl of DMSO and an aliquot was assayed for PBIA as described in the text.

Lipase Treatment

Four experimental conditions were used: (1) 200ng eq. of PBIL in 50μl ethanol +70μl of 1M Tris-HCl, pH 7.4+100μl of 2M NaCl+100μl of 1 mM Tris-HCl, pH 7.4+680μl of water; (2) same as (1) except 500μg of lipase was included; (3) 200ng eq. of PBIL in 50μl ethanol +70μl of 1 M Tris-HCl, pH 7.4+100μl of 2M NaCl +100 μl of 1 mM Tris-HCl, pH 7.4+10μl of 0.5M CaCl2+670μl of water; (4) same as (3) except 500μg of lipase was included.

Incubation was at 37° C. for 1 hour. Following incubation 3 ml chloroform/methanol (2:1) was added and mixed, and the organic layer was removed. To this, 2.5 ml of 0.9M NaCl was added and vigorously mixed. The samples were then centrifuged at 580xg for 10 minutes, the organic layer was removed, evaporated under nitrogen, suspended in 200μl DMSO and assayed for PBIA as described.

Lipoxygenase Treatment

Four incubation conditions were used: (1) 100ng eq. of PBIL in 30μl DMSO +1.45 ml of 0.2M Borate, pH 9+200μl of enzyme (lmg/ml in 0.2M Borate, pH 9); (2) same as (1) except enzyme was excluded; (3) 100ng eq. of PBIL in 30μl of DMSO +1.45 ml of PBS +200μl of enzyme (1 mg/ml in PBS); (4) same as (3) except enzyme was omitted.

Samples were incubated at 23° C. for 30 minutes. Following incubation 3 ml of 2:1 chloroform/methanol was added and mixed. Samples were then centrifuged at 580xg for 10 minutes, the bottom layer was removed, evaporated under nitrogen, suspended in 100µl DMSO and assayed for PBIA as described.

Hydrogenation Reaction

HPLC purified ligand, 300ng PDBu equivalent and monolinolein, 2mg/ml, were each separately dissolved in 1 ml hexane. Approximately 1-2mg of platinum oxide was then added to each tube. Hydrogen gas, was then gently bubbled into the tube bottoms for 1½ hours with gentle mixing performed at 15 minute intervals. The samples were then centrifuged at 580xg for 10 minutes in order to pellet the catalyst. The hexane was then transferred to another tube, the catalyst pellet was resuspended in 0.5 ml hexane, vortexed, centrifuged as above, and this hexane was added to that obtained from the first centrifugation. The hexane was evaporated under nitrogen and the residue was dissolved in 1 ml chloroform. One ml of 0.9M NaCl was then added, the tubes were vortexed, centrifuged as above, and the organic layer was removed. This was evaporated under nitrogen, dissolved in 125µl DMSO, and assayed for PBIA as described previously.

Acetylation Reaction

100ng PDBu eq. ligand was dried under nitrogen and to this 200µl of 1:1 acetic anhydride/pyridine was added. Incubation was at 37° C. for 2 hours. The samples were then frozen, lyophilized, and dissolved in DMSO for the PBIA assay as described.

Mild Alkali Treatment of Acetylated Lipid

Dry methanol was saturated to approximately 30 percent ammonia by bubbling in ammonia gas. One ml of this ammonia methanol was then added to the acetylated ligand and the sample was then incubated for 1 hour at 37° C. The methanol was then nitrogen evaporated, the sample was frozen, lyophilized and dissolved in DMSO for assay of PBIA.

Alkaline Methanolysis

Two hundred ng PDBu eq. ligand was dissolved in 2 ml of 1M NaOH in methanol and 2 ml of 1 M NH₄OH in methanol and incubated at 37° for 1 hour. A positive control consisting of 200ng PDBu equivalent ligand dissolved in 2 ml of methanol only was also included. All samples were then evaporated to dryness under nitrogen, 1 ml of CHCl₃ and 1 ml of 0.9M NaCl were added. Samples were thoroughly mixed and centrifuged at 580xg for 5 minutes. The organic layer was then removed and evaporated under nitrogen. The residue was dissolved in 100µl DMSO for PBIA determination as above.

Alkali Treatment

One ml of 0.1 N NaOH was added to 150ng PDBu equivalent ligand in 1 ml chloroform. This was vigorously mixed and then incubated for 2 hours at room temperature. The organic layer was removed, nitrogen evaporated and suspended in 100µl DMSO for PBIA assay as described.

RESULTS

Purification of Phorbol Binding Inhibiting Lipid (PBIL)

A summary of the purification of PBIL from murine intestine is presented in Table 1.

TABLE 1

| Fraction | PURIFICATION OF PHORBOL BINDING INHIBITING LIPID FROM MURINE INTESTINE | | | |
|---|---|---|---|---|
| | Total Lipid (mg) | Activity (ng PDBu equivalent) | Specific Activity (ng PDBu equivalent/mg) | Yield (%) |
| Crude lipid | 1905 | 28210 | 14.8 | 100 |
| Acetone extract | 653 | 27230 | 41.7 | 96.5 |
| Florisil chromatography | 117 | 12160 | 103.9 | 43.1 |
| First HPLC | 4.5 | 6380 | 1417.8 | 22.6 |
| Second HPLC | 3.6 | 5120 | 1422.2 | 18.1 |

A 96-fold purification with an 18% yield was achieved. The major inhibitory activity eluted from the column at 8% methanol in petroleum ether. Approximately 85% of activity was present in fraction 12. Dilinolein and monolinolein are eluted in fractions 10 and 12, respectively, under the experimental conditions described. When fraction 12 from the second HPLC step was rechromatographed a single peak of activity coinciding with $A_{235}$ absorbance peak was seen. The purification was also monitored by thin layer chromatography. As expected, each purification step from acetone extraction to the HPLC resulted in fewer components present. Four distinct lipids were seen in the acetone extract, 2 in the Florisil fraction VI, and only one in the HPLC purified fractions. The HPLC purified PBIL has the same $R_f$ value ($R_f$=0.05) as that of mono-glyceride monolinolein. The purified pancreatic and stomach PDIL also exhibited similar chromatographic characteristics.

Tissue and Species Distribution of PBIL

Various murine tissues were analyzed for PBIL concentration by preparing a dried acetone extract fraction, dissolving in DMSO and assaying for PBIA. The concentration is expressed as ng PDBu eq. per g wet tissue (see Table 2). Pancreas, intestine, stomach, spleen, thymus, lung, testicle, liver, kidney, skin, heart, thigh muscle, and brain, contained 353, 316, 174, 41, 33, 32, 26, 25, 24, 14, 14, 11 and 10ng PDBu eq./g wet tissue. No activity was detected in murine or human plasma. Thus, murine pancreas, intestine and stomach have exceptionally high amounts of PBIL.

TABLE 2

| DISTRIBUTION OF PHORBOL BINDING INHIBITING LIPID IN VARIOUS MOUSE TISSUES | |
|---|---|
| Tissue | Concentration (ng PDBu equivalent/g wet tissue) |
| Pancreas | 353 |
| Intestine | 316 |
| Stomach | 174 |
| Spleen | 41 |
| Thymus | 33 |
| Lung | 32 |

TABLE 2-continued
DISTRIBUTION OF PHORBOL BINDING INHIBITING LIPID IN VARIOUS MOUSE TISSUES

| Tissue | Concentration (ng PDBu equivalent/g wet tissue) |
| --- | --- |
| Testicle | 26 |
| Liver | 25 |
| Kidney | 24 |
| Skin | 14 |
| Heart | 14 |
| Muscle | 11 |
| Brain | 10 |
| Plasma | N.D.* |

*N.D. = Not Detectable.
Acetone extract was prepared from tissues and suspended in an appropriate amount of DMSO and assayed for PBIA as described in the text.

Pancreas, stomach, and intestines from various species (mouse, rat, hamster, guinea pig, and rabbit) were examined for the presence of PBIL (see Table 3). The pancreas of most of the species tested has the greatest concentration of PBIL. Thus, PBIL is widely distributed in rodent tissues.

TABLE 3
DISTRIBUTION OF PHORBOL BINDING INHIBITING LIPID IN DIFFERENT TISSUES OF VARIOUS SPECIES

| Species | Tissue | Concentration (ng PDBu equivalent/g wet tissue) |
| --- | --- | --- |
| Mouse | Intestine | 316 |
| | Pancreas | 353 |
| | Stomach | 174 |
| Rat | Intestine | 247 |
| | Pancreas | 1560 |
| | Stomach | 286 |
| Hamster | Intestine | 149 |
| | Pancreas | 1320 |
| | Stomach | 130 |
| Guinea Pig | Intestine | 195 |
| | Pancreas | 1040 |
| | Stomach | 195 |
| Rabbit | Intestine | 66 |
| | Pancreas | 780 |
| | Stomach | 65 |

There was not much difference in the amount of PBIL among intestine and pancreas of different strains of male or female mice. Intestinal and pancreatic tissue from mice of various ages (4–270 days) were tested for PBIL concentration. No marked age dependent alteration in PBIL concentration was observed.

Nature of Inhibition of PDBu Binding to Receptor by PBIL

The effect of PDBu concentration on the binding of PDBu to BMF in the absence and presence of purified intestinal lipid was determined. The binding assays were as described previously, using [$^3$H]PDBu and performed in the presence of 1, 24 and 36ng eq. 1 ml of PBIL. The inhibitory effect of PBIL was much greater at lower concentration of PDBu. As the concentration of PDBu was increased, decreasing the ratio of receptor to PDBu, PBIL-elicited effects lessened. Double reciprocal plots of binding in the absence and presence of PBIL were made. All three curves intersected the ordinate at the same point indicating that PBIL competitively inhibited PDBu binding to its receptors. Thus, Vmax remains the same in the absence and presence of PBIL. $K_m$ values for PDBu binding to receptor were increased in the presence of PBIL. Thus, PBIL reduced the affinity of PDBu for its receptors. The analysis of the data concerning the above determinations using Scatchard plot revealed the decrease of receptor affinity in the presence of PBIL. The PBIL-elicited inhibition of PDBu binding to receptor was not overcome by increasing the concentration of receptor protein, again indicating the competitive nature of inhibition. A dose response for the amount of PDBu bound with varying concentrations of intestinal PBIL at 4°, 23° and 37° C. was determined. PBIL inhibited the binding of PDBu to receptor in a dose dependent manner at various temperatures.

The purified milk PBIL, like intestinal PBIL, competitively inhibited the binding of $^3$H-PDBu to BMF in a dose dependent manner.

It was also found that PBIL reduces the binding of [$^3$H]PDBu to receptor protein purified to homogeneity.

Effect of PBIL on Protein Kinase Activity of Purified Receptor

Purified phorboid receptor from murine brain was purified to homogeneity and shown that the purified receptor is a serine-protein kinase (Shoyab, Cell Proliferation (CSH Laboratory) (1984) 11:253–262). The effect of PBIL on this protein kinase was tested. PBIL like of TPA stimulated the kinase activity about two-fold at concentrations between 0.4–0.8ng/PDBu eq. per ml. At higher concentration the kinase activity was inhibited (Table 4).

TABLE 4
EFFECT OF PBIL FROM MURINE INTESTINE ON PROTEIN KINASE ACTIVITY OF PURIFIED PHORBOID RECEPTOR

| Concentration (ng eq./0.25 ml) | PK Activity (CPM × 10$^{-4}$) | Percent of Control | Percent Stimulation |
| --- | --- | --- | --- |
| 0 | 22.7 | 100 | 0 |
| 0.02 | 26.2 | 115 | 15 |
| 0.05 | 32.5 | 143 | 43 |
| 0.10 | 49.4 | 194 | 94 |
| 0.20 | 43.5 | 192 | 92 |
| 0.50 | 33.0 | 145 | 45 |
| 1.0 | 29.1 | 128 | 28 |
| 2 | 21.1 | 93 | −7 |
| 5 | 16.6 | 73 | −27 |
| 10 | 15.1 | 67 | −33 |
| 20 | 14.3 | 63 | −37 |

The assay conditions were the same as described in the text except the indicated amount of PBIL and 25 ng of purified receptor protein (Shoyab, Cell Proliferation (CSH Laboratory) (1984) 11:253–262) were used.

Stimulation of Arachidonic Acid Cascade

The release of radioactivity into the medium from cells previously labeled with radioactive arachidonic was used as a measure of activation of eicosanoids pathway. The purified intestinal PBIL stimulated the release of radioactivity from cells into the medium in a dose- and time-dependent fashion. The maximum response was seen at lower doses of PBIL with increasing incubation time. PBIL from murine pancreas and intestine were also effective in this system, whereas PBIL from milk did not elicit this response. PBIL from all sources inhibited PDBu-receptor interaction. These results suggest that PBIL from murine tissues and from milk are structurally similar but not identical.

Chemical Characterization of PBIL

Various chemical and enzymatic treatments of intestinal PBIL were carried out in order to elucidate the structural features required for activity. Treatment with phospholipases did not affect the activity of lipid indicating non-phospholipid nature of PBIL. Lipase treatment inactivated the binding inhibiting activity suggesting the glyceride nature of PBIL. PBIA of lipid was not significantly altered by treatment with lipoxygenase. Catalytic hydrogenation of PBIL resulted in marked reduction of activity, indicating the presence of double bond(s) in the molecule needed for the PBIA. Acetylation of the lipid also reduced the activity of the molecule. When acetylated lipid was then treated with mild alkali, PBIA was restored. These results indicate that free hydroxyl-group(s) are present in the molecule and are essential for the activity. Alkaline methanolysis or strong alkali treatment of lipid made it markedly less active, providing more evidence that PBIL(s) are glycerides containing free hydroxyl group(s) and double bond(s). The results of various treatments and chromatographic behaviors of lipid molecules strongly suggested that PBIL(s) from murine tissues are monoglycerides with an unsaturated acyl group.

To further characterize EL1 and EL2, NMR, IR and GC-mass spectral analysis were conducted. IR and NMR data indicated the presence of ester bonds, hydroxyl groups and double bonds in the lipid molecules. Although EL1 was homogenous by HPLC and TLC, the GC-mass spectral analysis revealed that it was actually a mixture of 1- and 2-monoglycerides.

A number of lipids having structural similarity to those present in the analysis sample were assayed for their PBIA. The data are summarized in the following Table.

TABLE 5

| EFFECT OF VARIOUS LIPIDS ON THE BINDING OF PDBu TO ITS RECEPTOR | | |
|---|---|---|
| Compound | Concentration (nM) | Inhibition (%) |
| Methyl esters (Butyric to stearic acid) | 1 | 0 |
| Trilaurin | 0.4 | 11 |
| Trimystrin | 0.4 | 15 |
| Tripalmitin | 0.4 | −11 |
| Tripalmitin | 0.8 | −8 |
| 1,3-Dimyritin | 0.4 | 1 |
| 1-Monopalmitin | 0.8 | −6 |
| 1-Monomyristin | 0.4 | 0 |
| Glycerol | 0.4 | 0 |
| 1-Monopalmitin | 0.8 | −15 |
| 1,3-Dipalmitin | 0.8 | −12 |
| 1-Monoolein | 0.4 | 21 |
| 1-Monoolein | 0.8 | 63 |
| 1-Monopalmitolein | 0.4 | 36 |
| 1-Monopalmitolein | 0.8 | 82 |
| 1-Monolinolein | 0.2 | 39 |
| 1-Monolinolein | 0.4 | 82 |
| 1-Monolinolein | 0.8 | 94 |
| 1-Monolinolenin | 0.2 | 27 |
| 1-Monolinolenin | 0.4 | 74 |
| 1-Monolinolenin | 0.8 | 94 |
| 1-Monoarachidonin | 0.2 | 41 |
| 1-Monoarachidonin | 0.4 | 91 |
| 1-Monoarachidonin | 0.8 | 95 |
| 1,3-Diolein | 0.8 | 11 |
| 1,2-Diolein | 0.8 | 20 |
| 1,3-Dilinolein | 0.8 | 15 |
| Trilinolein | 0.8 | −1 |
| Linoleic acid-Na | 0.4 | 10 |

TABLE 5-continued

| EFFECT OF VARIOUS LIPIDS ON THE BINDING OF PDBu TO ITS RECEPTOR | | |
|---|---|---|
| Compound | Concentration (nM) | Inhibition (%) |
| Linoleic acid-Na | 0.8 | 15 |

PBIA assays were performed as described in the text.

Among various lipids tested, only monoglycerides with unsaturated long chain fatty acyl groups were markedly effective in inhibiting the binding of phorbol dibutyrate to its receptor, where the degree of inhibition increased with an increasing number of double bonds on the acyl chain.

Furthermore, it was shown that monolinolein like EL1 activated the arachidonic acid cascade in mink lung cells in a dose- and time-dependent manner.

The lipids described above may be employed in the stimulation of the arachidonic cascade by phorbol or ingenol receptor containing mammalian cells. Concentrations found to be effective are in the range of about 0.005 to 2ng/ml. The lipids may be present in an appropriate nutrient medium or administered to a particular tissue or organ in vitro in a physiologically acceptable medium.

It is evident from the above results, that the glycerides of the subject invention can find wide application in vitro. Since the compounds are simple aliphatic compounds, they may be readily synthesized in accordance with conventional ways, so as to provide an economic and readily available source of the compounds. They also may be used in affinity chromatography or binding for isolating cells or receptor proteins, in bioassays, and the like.

Although the foregoing invention has been described in some detail by way of illustration and example for purposes of clarity of understanding, it will be obvious that certain changes and modifications may be practiced within the scope of the appended claims.

What is claimed is:

1. A naturally occurring endogenous lipid composition wherein said lipid composition consists essentially of at least one substantially pure lipid, said lipid characterized by having phorbol and/or ingenol receptor binding activity, by having a purity wherein at least 90% of said lipid has said receptor binding activity, by having the ability to compete with phorbol dibutyrate for the phorbol dibutyrate membrane receptor, by being an unsaturated diglyceride having a higher fatty acid of 14 to 18 carbon atoms at position 1 and a lower fatty acid of 4 carbon atoms at position 2, and wherein said lipid composition is isolated from milk.

2. A naturally occurring endogenous lipid composition wherein said lipid composition consists essentially of at least one substantially pure lipid, said lipid characterized by having phorbol and/or ingenol receptor binding activity, by having a purity wherein at least 90% of said lipid has said receptor binding activity, by having the ability to compete with phorbol dibutyrate for the phorbol dibutyrate membrane receptor, by being an unsaturated diglyceride having a higher fatty acid of 14 to 18 carbon atoms at position 1 and a lower fatty acid of 6 carbon atoms at position 2, and wherein said lipid composition is isolated from milk.

* * * * *